United States Patent [19]
Galan Valdivia et al.

[11] Patent Number: 5,885,491
[45] Date of Patent: Mar. 23, 1999

[54] METHOD TO INCREASE THE STABILITY OF NANOCAPSULES DURING STORAGE THEREOF

[75] Inventors: Francisco Javier Galan Valdivia, Bardalona; Anna Coll Dachs, Barcelona; Nuria Carreras Perdiguer, Caldes De Montbui, all of Spain

[73] Assignee: Laboratorios Cusi, S.A., El Masnou, Spain

[21] Appl. No.: 900,036

[22] Filed: Jul. 24, 1997

Related U.S. Application Data

[63] Continuation of Ser. No. 604,887, Feb. 22, 1996, abandoned, which is a continuation of Ser. No. 454,500, May 30, 1995, abandoned, which is a continuation of Ser. No. 228,652, Apr. 18, 1994, abandoned.

[30] Foreign Application Priority Data

Apr. 20, 1993 [ES] Spain ...................................... 9300827

[51] Int. Cl.$^6$ ..................................................... B01J 13/04
[52] U.S. Cl. ......................... 264/4.1; 264/4.6; 428/402.2
[58] Field of Search ................... 264/4.1, 4.6; 428/402.2

[56] References Cited

U.S. PATENT DOCUMENTS

| | | | |
|---|---|---|---|
| 4,806,343 | 2/1989 | Carpenter et al. | 428/402.2 |
| 4,954,298 | 9/1990 | Yamamoto et al. | 264/4.6 |
| 5,049,322 | 9/1991 | Devissaguet et al. | 264/4.1 |
| 5,061,492 | 10/1991 | Okada et al. | 424/423 |
| 5,204,112 | 4/1993 | Hope et al. | 264/4.1 |
| 5,250,236 | 10/1993 | Gasco | 428/402.2 |
| 5,576,016 | 11/1996 | Amselem et al. | 424/450 |

OTHER PUBLICATIONS

Translation of Auvilliain et al. Jan. 1998 ("Lyophilization De Vecteurs Colloidaux Submiconiques", STP Pharma 5(11) 738–744, Jan. 1998.

"Lyophilization De Vecteurs Colloïdaux Submicroniques", By M. Auvillain, G. Cave, H. Fessi and J.P. Devissaguet, In S.T.P. Pharma 5 (11) 738–744, 1989. (with partial translation).

"Hackh's Chemical Dictionary, Fourth Edition", (McGraw–Hill Book Company, NY, NY) pp. 688, 1972 Month unknown.

*Primary Examiner*—Richard D. Lovering
*Assistant Examiner*—Daniel S. Metzmaier
*Attorney, Agent, or Firm*—Darby&Darby

[57] ABSTRACT

Methods of increasing storage stability of lipidic nucleus nanocapsules comprising adding a monosaccharide cryoprotective agent into the aqueous dispersion of the nanocapsules while maintaining gentle stirring until the same dissolves totally. Afterwards, freezing said dispersion thus obtained at a temperature of not less than −40° C. for about 2 to 4 hours, and the eliminating the water by heating progressively to a temperature of about 35° C. at reduced pressure, whereby a stable lyophilized product is obtained. The obtained product can be conveniently reconstituted by adding water or a more complex aqueous solution thereto. The nanocapsules have use in medicine, pharmacy, cosmetics, chemical industry, agriculture, and veterinary science.

14 Claims, No Drawings

METHOD TO INCREASE THE STABILITY OF NANOCAPSULES DURING STORAGE THEREOF

This is a continuation of application Ser No. 08/604,887, filed Feb. 22, 1996, now abandoned, which is a continuation of Ser. No. 08/454,500, filed May 30, 1995, now abandoned, which is a continuation of Ser. No. 08/228,652, filed Apr. 18, 1994, now abandoned.

TECHNICAL FIELD OF THE INVENTION

The present invention is in the technical field of lyophilization and, specifically, lyophilization of nanocapsules, submicron spheres formed by a lipidic nucleus surrounded by a polymeric membrane or a water insoluble substance. Lyophilization of nanocapsules makes it possible to increase their stability during storage thereof, in such a way that industrialization and subsequent marketing thereof for use in medicine, pharmacy, cosmetics, chemical industry, agriculture, veterinary science, etc. become possible.

PRIOR ART OF THE INVENTION

Colloidal systems of a polymeric nature in the form of nanocapsules and nanoparticles have been the object of numerous studies over the last few years. This is due to the fact that the use of this type of system for vehiculization of biologically active substances has brought about great expectations as a medium to reduce the doses of very toxic drugs and even to be directed towards a hypothetical target organ, among many other potential uses.

However, the use of biodegradable polymers, which would permit their optional use in medicine, veterinary science, etc., poses the problem of their degradation in an aqueous medium which would make storage thereof impossible in the form of a colloidal suspension for the time needed to market them. On the other hand, given the collidal nature of these systems, there is a tendency to the instability of the same which gives rise to an aggregation of initially individualized nanocapsules, and even a loss of the encapsulated substance by diffusion through the polymeric membrane during storage thereof.

Nanovesicular systems in the form of nanocapsules of a size smaller than on micrometer, formed by a solid or liquid lipidic nucleus containing one or more active substances, and surrounded by a membrane formed by a polymer or a water insoluble substance, have been described in different studies and inventions. However, suitable methods to increase the physical and physicochemical stability of the colloidal suspensions obtained have not been described, nor methods to prevent the degradation or dissolving of the polymers forming the wall, which would give rise to instabilization of the nanocapsules, causing them to break or the substance contained inside them from escaping.

It is obvious, that upon not having the stability of these systems solved for long periods of storage time is a very important limitation for their potential industrial use and marketing.

The patents BE-A 869107, FR-A 2504408 and FR-A 2515960 describe the preparation and use of biodegradable nanoparticles and nanocapsules obtained from the polymerization of alkyl cyanoacrylates and containing a biologically active substance.

European patent EP 480729A1 describes the microencapsulation of drops of oil of a size between 1 and 5 micra to orally administer a lyophilized product in the form of powder. Microencapsulation is described as a system to avoid degradation of unstable drugs in the conditions of the stomach.

The product object of this patent is used in the form of paste or powder. This differentiates it from the present invention which refers to a colloidal suspension smaller than 1 micron which is lyophilized and which can be rehydrated in order to be reconstituted as individualized nanocapsules, without producing aggregation of the same or an increase in size.

U.S. Pat. No. 4,247,411 describes lyophilization of liposomes to increase their stability, avoiding oxidation and contamination of the product. Conceptually and physically, liposomes are radically different from nanocapsules. Liposomes are vesicles formed by one or several bi-layers of phospholipids that surround an aqueous nucleus. Nanocapsules are formed by a polymeric wall that surrounds a lipidic type nucleus, usually an oil. Therefore, the cited patent refers to different products from those that are the object of the present invention.

The above cited patent uses filler substances such as: inorganic salts, colloidal silica, starch or aluminosilicates to avoid aggregation of the liposomes. Besides, as it is inferred from all the described examples, the lyophilization is carried out by freezing with liquid nitrogen, which makes industrialization thereof difficult to a large degree.

Unlike said patent, a monosaccharide is used in the method of the present invention as a cryorotective agent and the freezing is done to a temperature no lower than −40° C., which can be easily reached by any lyophilizer existing on the market. Therefore, this process does not need any special adaptation of the processes usually used on an industrial level.

French patent 8618444 describes the preparation and use of nanocapsules formed from preformed polymers and with different lipidic substances as the nucleus. Elimination of the solvents is done by lyophilization. In the single example in which reference is made to lyophilization thereof, use of trealose 20% is described, obtaining a product with a very high osmolality with regard to biological liquids such as blood, tears, etc.

It is very important to point out that in the cited patent, lyophilization is a process used exclusively to eliminate the solvents used during preparation and the purpose of this process is not to improve the stability of the systems obtained.

Subsequently, in the study published by the same authors "Lyophilization de vecteurs colloidaux submicroniques," STP Pharma 5(11) 738–744, 1989, M. Auvillain, G. Cavé, H. Fessi et J. P. Devissaguet, lyophilization of nanoparticles and of nanocapsules using different cryoprotective agents and various lyophilization conditions is studied. In this study, which explicitly refers to the above cited patent, the authors reach the conclusion that due to the fragility of the wall of the nanocapsules and to the composition thereof, use of approximately trealose 30% is necessary and besides, freezing down to temperatures between −70° C. and −196° C. using cooling mixtures or liquid nitrogen if one wishes to obtain a product with a correct reconstitution, has to be carried out. Therefore, the need to reach very low freezing temperatures makes the industrial use of the lyophilization process difficult and costly.

Use of trealose 30% gives rise to a product with an osmolality much higher than mOsm/Kg., which limits its use when an isotonic product is needed with regard to some biological liquids. Likewise, trealose is a very expensive product and its use at high concentrations significantly increases the cost of the final product.

DESCRIPTION OF THE INVENTION

The present invention proposed a method to increase the stability of nanocapsules being smaller that 0.5 micron of a polymeric nature by means of lyophilization. The lyophilization process that is proposed overcomes the disadvantages of prior ones, and it is useful to preserve nanocapsules made from polymers and oils, synthetic as well as natural ones.

Due to the structure of nanocapsules, formed by a lipidic nucleus, normally liquid, and by a fragile polymeric wall with a thickness of a few nanometers, it was to be expected that the use of high concentrations of a cryoprotective agent was necessary and in combination with a freezing temperature much lower than −40° C. to ensure total freezing of the system and to prevent the formation of large crystals that would affect the integrity of the nanocapsules.

However, it has been found, in accordance with the present invention, that when nanocapsules are lyophilized in the presence of a certain amount of a cryoprotective agent, especially a monosaccharide, such as glucose, by means of lyophilization it is possible to eliminate water from the suspension of nanocapsules and subsequently rehydrate the same without modifying the size of the same, without aggregates appearing or even, without a loss of the encapsulated substance being produced.

The freezing temperature required for the correct lyophilization of nanocapsules is approximately −40° C. and it is not necessary to use a cooling mixture or liquid nitrogen to reach lower temperatures. In this way, lyophilization of nanocapsules on an industrial level, and therefore, practical use thereof, is made easier to a large degree.

Use of a monosaccharide such as glucose at low concentrations makes it possible not to increase the cost of the product as in case when trealose is used and at the same time it makes it possible to obtain a product that upon being rehydrated can be hypotonic, isotonic or hypertonic in relation to biological liquids such as blood, tears, etc. This is a considerable advantage given that it is possible to modulate the final osmolality of the rehydrated product in terms of the use or way in which one wishes to administer the medicine.

Therefore, the present invention refers to a method to make it possible to increase the stability of nanocapsules during storage thereof in an economical easily industrializable way that makes it possible to obtain a rehydrated product maintaining its initial characteristics.

According to the present invention in the method chosen to carry out the process, the cryoprotective agent is added to the composition once the nanocapsules have been formed and it is kept gently stirred, 250 r.p.m. until it totally dissolves. This cryoprotective agent is added to prevent the nanocapsules from breaking, from their being crushed or aggregated, which would give rise to a heterogeneous product after lyophilization thereof; the cryoprotective agent is advantageously a monosaccharide such as glucose in concentrations from 3% (w/v) up to 10% (w/v.)

The product is dosed in vials or else placed on a tray and it is inserted in the lyophilizer where freezing is proceeded with for about 2 to 4 hours. Subsequently, water is eliminated by heating progressively up to +35° C. with a vacuum in the neighborhood of 0.2 mbars. The product that is obtained is a lyophilized material tablet formed by a fine powder of lyophilized nanocapsules. The lyophilized material tablet is reconstituted by adding a specific volume of water, buffer solution, electrolyte solution, viscosity modifying solution, etc. or any combination of the same, obtaining a colloidal suspension of characteristics practically identical to the initial ones.

The present invention also provides the composition of lyophilized nanocapsules obtained in the lyophilization process.

The copolymers that form the wall of the nanocapsules are synthetic or natural. In the case of synthetic polymers, for example, they may be poly(d,l)lactic acid, a semisynthetic polymer such as, for example, ethylcellulose, cellulose acetophthalate, etc.; acrylic acid copolymers and acrylic acid polymers (for example: Eudragit$^R$); lactic acid and glycolic acid copolymers; glycolide derivatives (propiolactone, butyrolactone, pivalolactone, epsiloncaprolactone derivatives, etc.); maleic acid and benzyl maleate copolymers, polysaccharides, etc. In the case of natural ones, for example, gelatin, arabic gum, etc.

The substance forming the lipidic nucleus can be for example a hydrogenated oil, a natural oil, natural oil derivatives such as coconut oil, castor oil, etc., a synthetic oil, ethoxylated oleic glycerides, diethylene glycol monoethyl ether, $C_8$–$C_{10}$ ethoxylated glycerides, phospholipids, petroleum derivatives, etc.

The substance contained in the nucleus of the nanocapsules can be a biologically active substance such as a medicinal active principle, an active principle precursor, a contrast substance, a pigment, a dye, an adhesive, a lubricant, etc. The substance contained in the nucleus can be dissolved or dispersed in the same.

In the composition that is subjected to the lyophilization process, the continuous phase that surrounds the nanocapsules is an aqueous phase that contains a natural surface active agent such as lecithins, an anionic synthetic surface active agent such as sodium or cationic lauryl sulfate, for example a quaternary or non-ionic ammonium such as for example ethoxylated sorbitan esters, fatty alcohol esters and polyoxyethylene glycol esters, polyoxyethylene polyoxypropylene glycols or else a suspension agent such as dextrane, polyvinyl alcohol, etc. The ratio between the weight of the nanocapsules and the weight of the aqueous continuous phase of the dispersion is generally 0.01 to 0.5

The final lyophilized product can be rehydrated, compressed, extruded or can form part of a more complex composition.

EMBODIMENTS OF THE INVENTION

The present invention is additionally illustrated by means of the following examples, which must not be considered restrictive of the scope of the same which is defined by the attached set of claims.

EXAMPLE 1

POLYEPSILONCAPROLACTONE-MIGLYOL 840® NANOCAPSULES 0.996 g. of Lutrol F68$^R$ are dissolved in 50 ml. of deionized water and filtered through 0.22 μm (AQUEOUS PHASE). 0.250 g of polyepsiloncaprolactone are dissolved in 25 ml. of acetone using ultrasound for 5 minutes and 0.250 ml. of Miglyol 840® (Dynamit Nobel) (ORGANIC PHASE) are added. The organic phase is added to the aqueous phase is added to the aqueous phase with gentle stirring. Once it has been totally added, the recently formed colloidal suspension is placed in a rotavapor where the organic solvent is eliminated under vacuum and the suspension is concentrated to a final volume of 30 ml. The pH is adjusted to 7 with NaOH 0.01N.

Glucose is added up to a concentration of 2, 3, 4 or 5%; it is dosed in glass vials, it is frozen down to −40° C. and the water is eliminated by increasing the temperature up to about 35° C. and with reduced pressure of 0.2 to 0.4 mbars for 12–14 hours. The final product is a white and compact tablet of lyophilized product. The lyophilized product is rehydrated with deionized water obtaining a colloidal suspension with the same characteristics as before lyophilization thereof.

The average particle size and the polydispersity are measured by photonic correlation spectroscopy and potential Z by electrophoretic mobility (Zetasizer 3, Malvern Instruments.) The determinations are made before lyophilizing and after rehydrating the lyophilized product. The results obtained are given in the following table:

| % Glucose | Average (nm) size | | R Tf/Ti | Polydispersity | | Potential Z | |
|---|---|---|---|---|---|---|---|
| | Before lyophi. | After lyophi. | | Before lyophi. | After lyophi. | Before lyophi. | After lyophi. |
| 2 | 294.3 | 326.9 | 1.11 | 0.146 | 0.058 | −16.70 | −19.38 |
| 3 | 297.8 | 313.7 | 1.05 | 0.132 | 0.097 | −16.41 | −15.15 |
| 4 | 312.8 | 310.4 | 0.99 | 0.084 | 0.161 | −16.38 | −15.55 |
| 5 | 305.0 | 308.9 | 1.01 | 0.110 | 0.156 | −17.15 | −13.83 |

Tf/Ti = Average size after lyophilizing/Average size before lyophizing

EXAMPLE 2

POLYEPSILONCAPROLACTONE-EDENOR TI5® NANOCAPSULES

The technique described in Example 1 is used, but Miglyol 840® (Dynamit Nobel) is replaced by Edenor TiO5® (Pulcra.) The average particle size and polydispersity are measured by photonic correlation spectroscopy and potential Z by electrophoretic mobility (Zetasizer 3, Malvern Instruments.) The determinations are carried out before lyophilizing and after rehydrating the lyophilized product. The results obtained are given in the following table:

| % Glucose | Average (nm) size | | R Tf/Ti | Polydispersity | | Potential Z | |
|---|---|---|---|---|---|---|---|
| | Before lyophi. | After lyophi. | | Before lyophi. | After lyophi. | Before lyophi. | After lyophi. |
| 2 | 281.4 | 287.7 | 1.02 | 0.064 | 0.149 | −23.31 | −22.65 |
| 3 | 289.8 | 271.9 | 0.94 | 0.126 | 0.142 | −23.34 | −21.89 |
| 4 | 274.8 | 260.5 | 0.95 | 0.186 | 0.203 | −22.69 | −22.04 |
| 5 | 278.4 | 267.0 | 0.96 | 0.167 | 0.155 | −23.20 | −21.19 |

Tf/Ti = Average size after lyophilizing / Average size before lyophilizing

EXAMPLE 3

POLYEPSILONCAPROLACTONE-EDENOR TiO5® NANOCAPSULES

The technique described in Example 1 is used, but Miglyol 840® (Dynamit Nobel) is replaced by Edenor TiO5® (Pulcra) and 0.750 ml. are used, instead of 0.250 ml. Only glucose 6% is used as the cryoprotective agent. The average particle size and polydispersity are measured by photonic correlation spectroscopy and potential Z by electrophoretic mobility (Zetasizer 3, Malvern Instruments.) The determinations are carried out before lyophilizing and after rehydrating the lyophilized product. The results obtained are given in the following table:

| % Glucose | Average (nm) size | | R Tf/Ti | Polydispersity | | Potential Z | |
|---|---|---|---|---|---|---|---|
| | Before lyophi. | After lyophi. | | Before lyophi. | After lyophi. | Before lyophi. | After lyophi. |
| 6 | 282.8 | 270.9 | 0.96 | 0.174 | 0.163 | −27.63 | −23.58 |

Tf/Ti = Average size after lyophilizing / Average size before lyophilizing

EXAMPLE 4

POLYLACTIC-GLYCOLIC 75:25-MIGLYOL 840® NANOCAPSULES

The technique described in Example 1 is used but polyepsiloncaprolactone (Sigma-Aldrich) is replaced by the polylactic-glycolic copolymer 75:25 (Boerhinger Ingelheim.) The average particle size and polydispersity are measured by photonic correlation spectroscopy and potential Z by electrophoretic mobility (Zetasizer 3, Malvern Instruments.) The determinations are carried out before lyophilizing and after rehydrating the lyophilized product. The results obtained are given in the following table:

| % Glucose | Average (nm) size | | R Tf/Ti | Polydispersity | | Potential Z | |
|---|---|---|---|---|---|---|---|
| | Before lyophi. | After lyophi. | | Before lyophi. | After lyophi. | Before lyophi. | After lyophi. |
| 2 | 295.8 | 305.3 | 1.03 | 0.185 | 0.180 | −15.58 | −12.56 |
| 3 | 302.9 | 296.7 | 0.98 | 0.170 | 0.171 | −13.91 | −12.12 |
| 4 | 288.5 | 289.3 | 1.00 | 0.212 | 0.171 | −13.55 | −10.67 |
| 5 | 289.5 | 275.6 | 0.95 | 0.196 | 0.086 | −13.48 | −10.45 |

Tf/Ti = Average size after lyophilizing / Average size before lyophilizing

EXAMPLE 5

POLYLACTIC-GLICOLIC 75:25 EDENOR TiO5® NANOCAPSULES

The technique described in Example is used, but Miglyol 840® (Dynamit Nobel) is replaced by Edenor TiO5® (Pulcra.) The average particle size and polydispersity are measured by photonic correlation spectroscopy and potential Z by electrophoretic mobility (Zetasizer 3, Malvern Instruments.) The determinations are carried out before lyophilizing and after rehydrating the lyophilized product. The results obtained are given in the following table:

| % Glucose | Average (nm) size | | R Tf/Ti | Polydispersity | | Potential Z | |
|---|---|---|---|---|---|---|---|
| | Before lyophi. | After lyophi. | | Before lyophi. | After lyophi. | Before lyophi. | After lyophi. |
| 2 | 249.2 | 278.4 | 1.12 | 0.197 | 0.199 | −22.34 | −19.62 |
| 3 | 252.5 | 270.2 | 1.07 | 0.127 | 0.149 | −20.80 | −19.39 |
| 4 | 249.8 | 247.8 | 0.99 | 0.094 | 0.093 | −20.87 | −18.95 |
| 5 | 239.2 | 239.0 | 0.99 | 0.168 | 0.122 | −21.20 | −19.96 |

Tf/Ti = Average size after lyophilizing / Average size before lyophilizing

EXAMPLE 6

POLYEPSILONCAPROLACTONE-INDOMETHACIN 0.1% NANOCAPSULES 3.32 g. of Lutrol F68 are dissolved in 200 ml. of deionized water and filtered through 0.22μ (AQUEOUS PHASE)

0.415 g. of polyepsiloncaprolactone are dissolved in 100 ml. of acetone using ultrasound for 5 minutes. 0.101 g. of indomethacin are dissolved in 0.830 ml. of Miglyol 812$^R$ and are added to the previous acetone solution (ORGANIC PHASE:) The organic phase is added to the aqueous phase with stirring. Once it has been totally added, the recently formed colloidal suspension is placed in a rotavapor where the organic solvent (acetone) is eliminated under vacuum and the product is concentrated to a final volume of 100 ml. The final colloidal suspension has its ph adjusted to 5.5 with NaOH 0.01N. The resulting concentrations are:

| | |
|---|---|
| Lutrol F68 ® | 3.32% (w/v) |
| Poly-E-caprolactone | 0.415% (w/v) |
| Miglyol 812 ® | 0.83% (w/v) |
| Indomethacin | 0.10% (w/v) |

Glucose is added up to a concentration of 3, 4 or 5%; it is dosed in glass vials and it is frozen down to −40° C. It is lyophilized with a vacuum between 0.2–0.4 mbar approximately for 12–16 hours until a final temperature of about 30° C. is reached. The final product is a slightly yellow compact tablet. After reconstituting with 2 ml. of purified water, a colloidal suspension with the same characteristics as the initial one (before lyophilizing) is obtained.

The average particle size and polydispersity are measured by photonic correlation spectroscopy and potential Z by electrophoretic mobility (Zetasizer 3, Malvern Instruments.) The determinations are carried out before lyophilizing and after rehydrating the lyophilized product. The results obtained are given in the following table:

| | Average (nm) size | | | Polydispersity | | Potential Z | |
|---|---|---|---|---|---|---|---|
| % Glu-cose | Before lyophi. | After lyophi. | R Tf/Ti | Before lyophi. | After lyophi. | Before lyophi. | After lyophi. |
| 3 | 219.95 | 217.8 | 0.99 | 0.072 | 0.140 | −12.71 | −10.44 |
| 4 | 218.85 | 218.1 | 0.99 | 0.088 | 0.116 | −14.42 | −10.12 |
| 5 | 221.45 | 210.9 | 0.95 | 0.124 | 0.159 | −14.20 | −10.25 |

Tf/Ti = Average size after lyophilizing / Average size before lyophilizing

After ultrafiltration in a centrifuge at 2500 rpm, the amount of indomethacinin the filtrate is determined. The amount of indomethacin in the total formula less the amount of indomethacin in the filtrate, determined by high resolution liquid chromatography corresponds to the amount of indomethacin included in the nanocapsules that is kept at the same level before and after lyophilization, just as it is shown in the following table:

| % ENCAPSULATION INDOMETHACIN | | |
|---|---|---|
| % Glucose | Before lyophilizing | After lyophilizing |
| 3 | 91.05 | 89.30 |
| 4 | 91.05 | 88.95 |
| 5 | 91.05 | 89.10 |

EXAMPLE 7

1.992 g. of Lutrol F68® are dissolved in 100 ml. of deionized water and filtered through 0.22μ (AQUEOUS PHASE.) 0.498 g. of polyepsiloncaprolactone are dissolved in 50 ml. of acetone using ultrasound for 5 minutes. 0.1217 g. of carteolol base are dissolved in 0.96 ml. of Edenor TiO5® and are added to the previous acetone solution (ORGANIC PHASE.)

The organic phase is added to the aqueous phase with stirring. Once it has been totally added, the recently formed colloidal suspension is placed in a rotavapor where the organic solvent (acetone) is eliminated under vacuum and the product is concentrated to a final volume of 60 ml. The final colloidal suspension has its pH adjusted to 7 with HCl 0.01N. The resulting concentrations are:

| | |
|---|---|
| Lutrol F68 ® | 3.32% (w/v) |
| Poly-E-caprolactone | 0.83% (w/v) |
| Edenor TiO$_5$ ® | 1.6% (w/v) |
| Carteolol base | 0.2% (w/v) |

Glucose is added to a concentration of 3, 4, 5, 6 or 7%; it is dosed in vials and it is frozen down to −40° C. It is lyophilized with a vacuum between 0.2–0.4 mbar approximately for 12–16 hours until a final temperature of about 30° C. is reached. The final product is a white compact tablet in all cases. After reconstituting with 2 ml. of purified water a colloidal suspension with the same characteristics as the initial one (before lyophilizing) is obtained.

The average size and polydispersity of the nanocapsules obtained are measured by photonic correlation spectroscopy and potential Z by electrophoretic mobility (Zetasizer 3) and, just like the other physicochemical controls, they are determined before lyophilizing and once the product has been reconstituted.

| | Average (nm) size | | | Polydispersity | | Potential Z | |
|---|---|---|---|---|---|---|---|
| % Glu-cose | Before lyophi. | After lyophi. | R Tf/Ti | Before lyophi. | After lyophi. | Before lyophi. | After lyophi. |
| 3 | 245.7 | 262.7 | 1.07 | 0.264 | 0.182 | −26.91 | −21.64 |
| 4 | 259.9 | 242.9 | 0.93 | 0.135 | 0.187 | −21.505 | −21.87 |
| 5 | 256.9 | 246.7 | 0.96 | 0.162 | 0.146 | −21.905 | −19.91 |
| 6 | 259.9 | 241.4 | 0.93 | 0.107 | 0.177 | −19.33 | −19.96 |
| 7 | 258.8 | 241.9 | 0.93 | 0.177 | 0.150 | −20.11 | −20.01 |

Tf/Ti = Average size after lyophilizing / Average size before lyophilizing

After ultrafiltration in a centrifuge at 2500 rpm, the amount of carteolol base in the filtrate is determined. The amount of carteolol in the total formula less the amount of carteolol in the filtrate, determined by high resolution liquid chromatography, corresponds to the amount of carteolol base included in the nanocapsules which is kept at the same level before and after lyophilization, just as it is shown in the following table:

| % ENCAPSULATION CARTEOLOL BASE | | |
|---|---|---|
| % Glucose | Before lyophilizing | After lyophilizing |
| 3 | 82 | 83 |
| 4 | 82 | 82.5 |
| 5 | 82 | 83 |
| 6 | 82 | 83 |
| 7 | 82 | 82.5 |

We claim:

1. A method to increase the stability of nanocapsules during storage thereof wherein the nanocapsules are smaller than 0.5 micron and are formed with a lipid nucleus of a natural or synthetic origin and contain at least one chemically or biologically active substance surrounded by a polymeric wall of a synthetic or natural origin; comprising adding a cryoprotective agent in an aqueous dispersion of the nanocapsules while stirring until the monosaccharide cryoprotective agent in a concentration between 2 and 10% dissolves, subjecting the dispersion thus obtained to a temperature no lower than −40° C. for about 2 to 4 hours, and eliminating water by heating progressively to a temperature of about 35° C. at a reduced pressure, thereby providing a stable lyophilized product in the form of a fine powder.

2. The method of claim 1 wherein the cryoprotective agent is glucose.

3. The method of claim 1 wherein the ratio between the weight of nanocapsules and the weight of the aqueous phase of the dispersion is 0.01 to 0.05.

4. The method of claim 1 wherein the substance contained in the nucleus of the nanocapsules is a biologically active substance selected from the group consisting of a medicinal active principle, an active principle precursor, a cosmetic substance, a radioactive substance, a contrast substance, a pigment, a dye, an adhesive or a lubricant.

5. The method of claim 1 wherein the polymer that forms the wall that surrounds the nucleus of the nanocapsules is poly(d,l)lactic acid, ethylcellulose, cellulose acetophthalate, acrylic acid copolymer, an acrylic acid polymer, lactic acid and glycolic acid copolymer, glycolide derivatives selected from the group consisting of propiolactone, butyolactone, pivalolactone and epsiloncaprolactone; maleic acid and benzyl maleate copolymers, a polysaccharide, a polypeptide, gelatin or arabic gum.

6. The method of claim 1 wherein the substance that forms the lipidic nucleus of the nanocapsules is a natural oil, a synthetic oil, a hydrogenated oil, ethoxylated oleic glycerides; $C_8$–$C_{10}$ ethoxylated glycerides, phospholipids, a petroleum derivative, diethylene glycol monoethyl ether, or a mixture of any of the foregoing.

7. The method according to claim 6 wherein the lipidic nucleus of the nanocapsules is selected from the group consisting of coconut oil and castor oil.

8. The method of claim 1 wherein the continuous phase that surrounds the nanocapsules is an aqueous phase that contains a surface active agent or a suspension agent.

9. The method of claim 8 wherein the surface active agent contained in the aqueous phase is a lecithin, an anionic synthetic surface active agent, a cationic surface active agent or a non-ionic surface active agent.

10. The method of claim 9 wherein the non-ionic surface active agent contained in the aqueous phase is a poloxamer.

11. The method of claim 10 wherein the poloxamer is a concentration between 2.5. and 10%.

12. The method of claim 8 wherein the suspension agent is a polysaccharide, a polyvinyl alcohol or a polypeptide.

13. The method according to claim 1 including the further step of rehydrating of the lyophilized product is carried out to obtain the aqueous dispersion of nanocapsules.

14. The method according to claim 13 wherein the lyophilized product is rehydrated with water or a more complex aqueous solution, selected from the group consisting of buffer solutions, electrolyte solutions, viscosity modifying solutions and mixtures of any of the foregoing.

* * * * *

UNITED STATES PATENT AND TRADEMARK OFFICE
CERTIFICATE OF CORRECTION

PATENT NO. : 5,885,491
DATED : March 23, 1999
INVENTOR(S) : Francisco Javier Galan Valdivia It is certified that error appears in the above-identified patent and that said Letters Patent is hereby corrected as shown below:

ON THE TITLE PAGE:

Item, [75] Inventors, change "BARDALONA to --BADALONA--.

Signed and Sealed this

Seventh Day of September, 1999

Attest:

Q. TODD DICKINSON

*Attesting Officer*     *Acting Commissioner of Patents and Trademarks*